(12) United States Patent  (10) Patent No.: US 8,247,241 B2
Hirai et al.  (45) Date of Patent: Aug. 21, 2012

(54) METHOD FOR DETECTING TARGET COMPOUND

(75) Inventors: Hiroyuki Hirai, Kanagawa (JP);
Masayoshi Kojima, Kanagawa (JP);
Isao Tsuyuki, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 936 days.

(21) Appl. No.: 11/723,634

(22) Filed: Mar. 21, 2007

(65) Prior Publication Data

US 2007/0224705 A1    Sep. 27, 2007

(30) Foreign Application Priority Data

Mar. 22, 2006   (JP) ................................ 2006-079734

(51) Int. Cl.
*G01N 33/553* (2006.01)
(52) U.S. Cl. ... 436/526; 435/7.1; 435/283.1; 435/287.1; 435/287.2; 436/518; 436/524; 436/525; 436/806; 436/149; 436/150
(58) Field of Classification Search .................. 435/7.1, 435/283.1, 287.1, 287.2; 436/518, 524, 526, 436/525, 806, 149, 150
See application file for complete search history.

(56) References Cited

U.S. PATENT DOCUMENTS

| 5,345,591 | A | 9/1994 | Tsurumaki et al. |
| 5,508,164 | A | 4/1996 | Kausch et al. |
| 5,665,582 | A | 9/1997 | Kausch et al. |
| 5,965,283 | A * | 10/1999 | Solin et al. ............. 428/812 |
| 5,981,297 | A * | 11/1999 | Baselt ..................... 436/514 |
| 6,736,978 | B1 * | 5/2004 | Porter et al. ............ 210/695 |
| 6,858,439 | B1 * | 2/2005 | Xu et al. ................. 436/518 |
| 7,410,811 | B2 * | 8/2008 | Lin et al. ................ 436/526 |
| 2003/0124745 | A1 | 7/2003 | Chen |
| 2005/0035757 | A1 | 2/2005 | Prins et al. |
| 2005/0036921 | A1 | 2/2005 | Nagasawa et al. |
| 2005/0087000 | A1 * | 4/2005 | Coehoorn et al. ........ 73/53.01 |

FOREIGN PATENT DOCUMENTS

| JP | 05-022181 A | 1/1993 |
| JP | 5-292971 A | 11/1993 |
| JP | 6-510363 A | 11/1994 |

(Continued)

OTHER PUBLICATIONS

Shigeru Tamatsukuri, "Molecular Diagnosis with Magnetic Micro Particles," *Bio Industry*, 2004, vol. 21, No. 8, pp. 39-47 (with partial English translation, cited in specification).

(Continued)

*Primary Examiner* — Melanie J Yu
(74) *Attorney, Agent, or Firm* — Buchanan Ingersoll & Rooney PC

(57) ABSTRACT

According to an aspect of the invention, there is provided a method for detecting a target compound including: injecting a test liquid containing a target compound into a colloid solution of magnetic nano-particles having an average particle diameter of 50 nm or less to allow the target compound to bind to the magnetic nano-particles, thereby forming bound magnetic nano-particles having a diameter of 100 nm or more; and bringing a dispersion liquid containing the bound magnetic nano-particles in proximity to a magnetic sensor including at least a magnetoresistive (MR) element and a permanent magnet while measuring the change in magnetic resistance to selectively detect the bound magnetic nano-particles, thereby indirectly detecting the target compound.

12 Claims, 6 Drawing Sheets

FOREIGN PATENT DOCUMENTS

| | | |
|---|---|---|
| JP | 10-078409 A | 3/1998 |
| JP | 2001-133458 A | 5/2001 |
| JP | 2002-060436 A | 2/2002 |
| JP | 2003-523185 A | 8/2003 |
| JP | 2004-503775 | 2/2004 |
| JP | 2004-530103 A | 9/2004 |
| JP | 2005-046651 A | 2/2005 |
| JP | 2005-513485 A | 5/2005 |
| JP | 2005-288254 A | 10/2005 |
| WO | 00/05357 A1 | 2/2000 |
| WO | WO 01/96857 A2 | 12/2001 |
| WO | 02/16528 A1 | 2/2002 |
| WO | 02/16571 A1 | 2/2002 |

OTHER PUBLICATIONS

Official Action dated Mar. 29, 2011, issued by the Japanese Patent Office in corresponding patent application No. 2006-079734, and English language translation of the Official Action.

Office Action (Notice of Reasons for Rejection) issued by the Japanese Patent Office issued in corresponding Japanese Patent Application No. 2006-079734 dated Jun. 21, 2011, and English translation thereof.

* cited by examiner

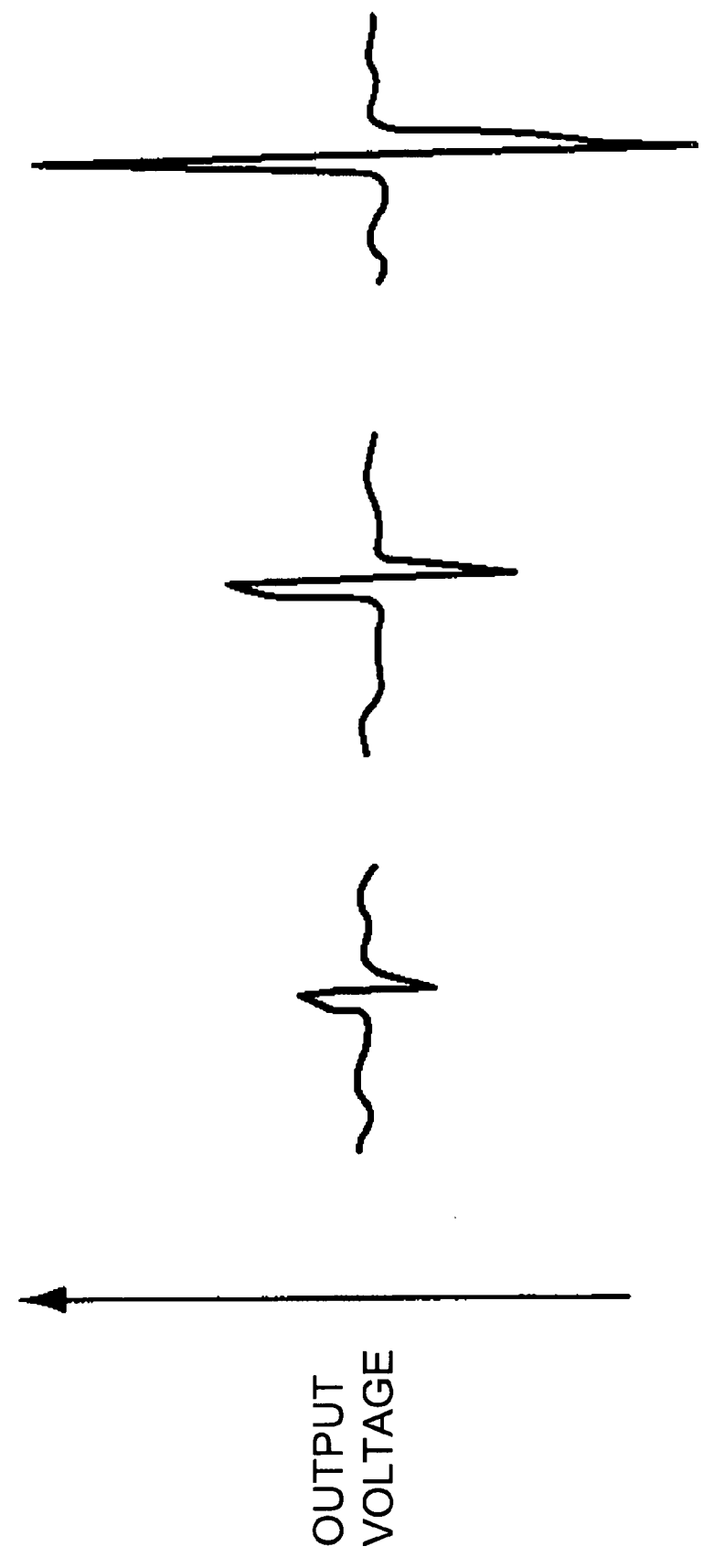

METHOD FOR DETECTING TARGET COMPOUND

CROSS-REFERENCE TO RELATED APPLICATION

This application claims priority under 35 USC 119 from Japanese Patent Application No. 2006-079734, the disclosure of which is incorporated by reference herein.

BACKGROUND OF THE INVENTION

1. Field of the Invention

The present invention relates to a method for detecting a target compound using magnetic nano-particles, and in particular to a method for selectively detecting bound magnetic nano-particles to which the target compound is bound in a liquid mixture in which magnetic nano-particles to which the target compound is bound and magnetic nano-particles to which the target compound is not bound are mixed together.

2. Description of the Related Art

Means using magnetic fine particles having a size of several μm have been proposed as means for effectively collecting a minute amount of a target compound. Examples of commercially available products include DYNABEADS, which are polystyrene beads (with a particle diameter of several μm) in which ferrite fine particles are dispersed. Such magnetic fine particles are used as precise detection means for detecting biological substances since the magnetic fine particles can be simply and effectively collected using an external magnetic field (for example, see International Publication No. WO 00/05357, Japanese Patent Application Laid-Open (JP-A) No. 5-292971, Japanese Patent Application National Publication (Laid-Open) No. 2003-523185, and Bio Industry, 2004, Vol. 21, No. 8, pp. 39-47). However, although the responsiveness to a magnet is good since the particle diameter is large, the adsorption amount and analytical sensitivity of desired substances (target compounds) are not sufficient. On the other hand, there is another problem in that separation with a magnet becomes difficult when the particle diameter is reduced to several tens of nanometers or less since the ferromagnetism changes to superparamagnetism. Thermal stimulation responsive magnetic nano-particles taking advantage of polymers having a lower critical solution temperature (LCST) or an upper critical solution temperature (UCST) have been proposed as means for effectively separating a target compound using magnetic nano-particles (see, for example, International Publication Nos. WO 02/16571 and WO 02/16528, and JP-A No. 2002-60436).

However, in order to efficiently detect a target compound using the magnetic nano-particles responsive to external stimulation such as heat, a so-called "washing" step is essential, wherein the target compound bound to the magnetic nano-particles is once trapped by a magnetic force, and the target compound bound to the magnetic nano-particles is selectively extracted by washing other samples away.

SUMMARY OF THE INVENTION

According to an aspect of the invention, there is provided a method for detecting a target compound comprising:

injecting a test liquid containing a target compound into a colloid solution of magnetic nano-particles having an average particle diameter of 50 nm or less to allow the target compound to bind to the magnetic nano-particles, thereby forming bound magnetic nano-particles having a diameter of 100 nm or more; and bringing a dispersion liquid containing the bound magnetic nano-particles in proximity to a magnetic sensor comprising at least a magnetoresistive (MR) element and a permanent magnet while measuring the change in magnetic resistance to selectively detect the bound magnetic nano-particles, thereby indirectly detecting the target compound.

BRIEF DESCRIPTION OF THE DRAWINGS

FIG. 6 is a graph obtained by measuring the output voltage of the sample in Example 1.

DETAILED DESCRIPTION OF THE INVENTION

A method for detecting a target compound according to the invention comprises: injecting a test liquid containing a target compound into a colloid solution of magnetic nano-particles having an average particle diameter of 50 nm or less to allow the target compound to bind to the magnetic nano-particles, thereby forming bound magnetic nano-particles having a diameter of 100 nm or more; and bringing a dispersion liquid containing the bound magnetic nano-particles in proximity to a magnetic sensor comprising at least a magnetoresistive (MR) element and a permanent magnet while measuring the change in magnetic resistance to selectively detect the bound magnetic nano-particles, thereby indirectly detecting the target compound.

A specific example of the method for detecting a target compound according to the invention comprises: injecting a test liquid containing a target compound into a colloid solution of magnetic nano-particles having an average particle diameter of 50 nm or less to allow the target compound to bind to the magnetic nano-particles, thereby forming bound magnetic nano-particles having a diameter of 100 nm or more; concentrating the formed bound magnetic nano-particles by magnetic separation, thereby obtaining a concentrated dispersion liquid of the bound magnetic nano-particles; and bringing the concentrated dispersion liquid in proximity to a magnetic sensor comprising at least a magnetoresistive (MR) element and a permanent magnet while measuring the change in magnetic resistance to selectively detect the bound magnetic nano-particles, thereby indirectly detecting the target compound.

A more specific example of the method for detecting a target compound according to the invention comprises: injecting from 0.1 to 1000 μL of a test liquid containing a target compound into a colloid solution of magnetic nano-particles having an average particle diameter of 50 nm or less, the colloid solution flowing at a flow rate from 0.001 to 100 mL/minute in a flow channel having a cross section from 10 to $10^7$ μm$^2$, to allow the target compound to bind to the magnetic nano-particles, thereby forming bound magnetic nano-particles having a diameter of 100 nm or more; and bringing the resulting liquid mixture containing the bound magnetic nano-particles in proximity to a magnetic sensor comprising at least a magnetoresistive (MR) element and a permanent magnet while measuring the change in magnetic resistance to selectively detect the bound magnetic nano-particles, thereby indirectly detecting the target compound.

Figure 1:
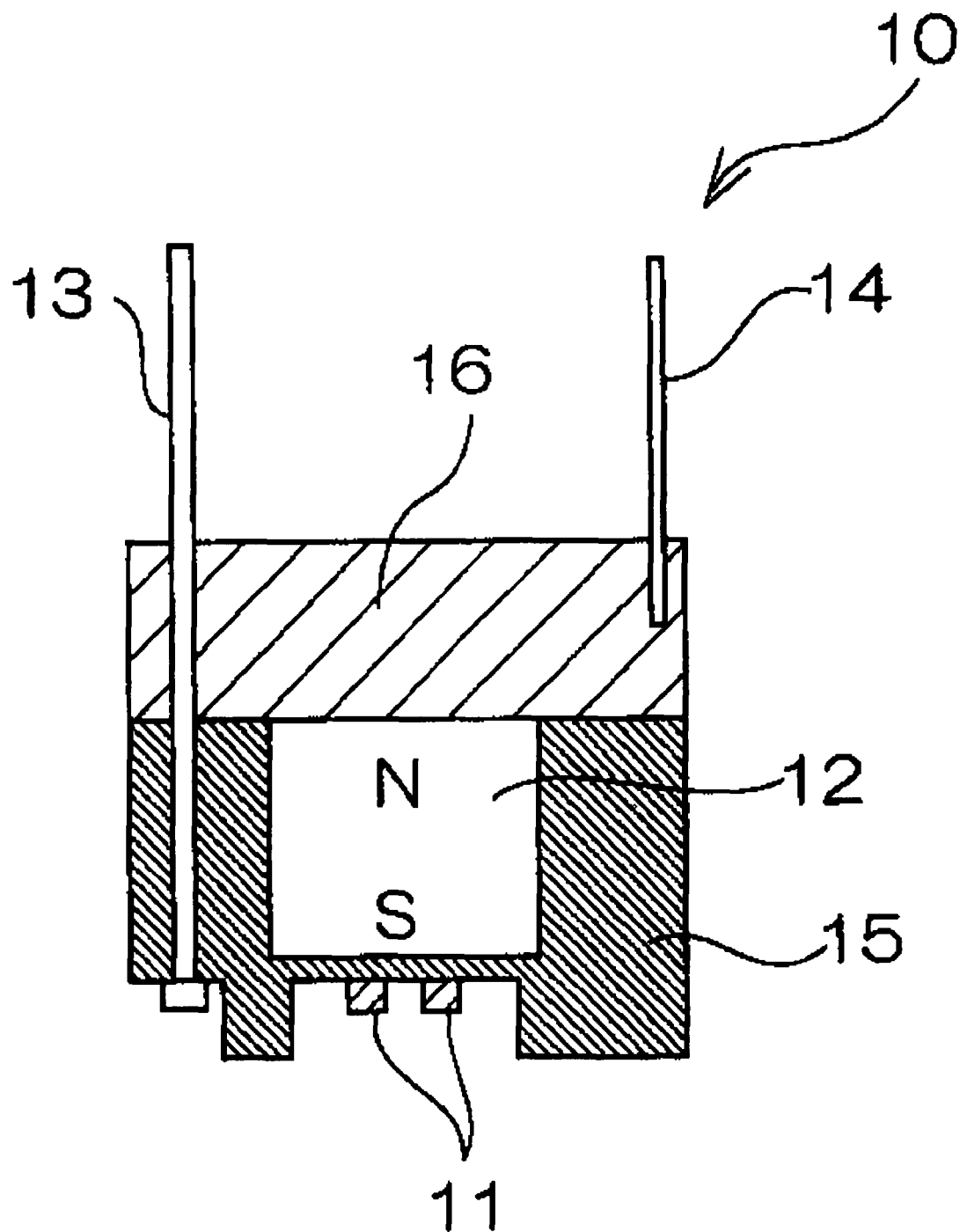
FIG. 1 is a cross section of a magnetic sensor used for a detection method of the invention.
Figure 2:
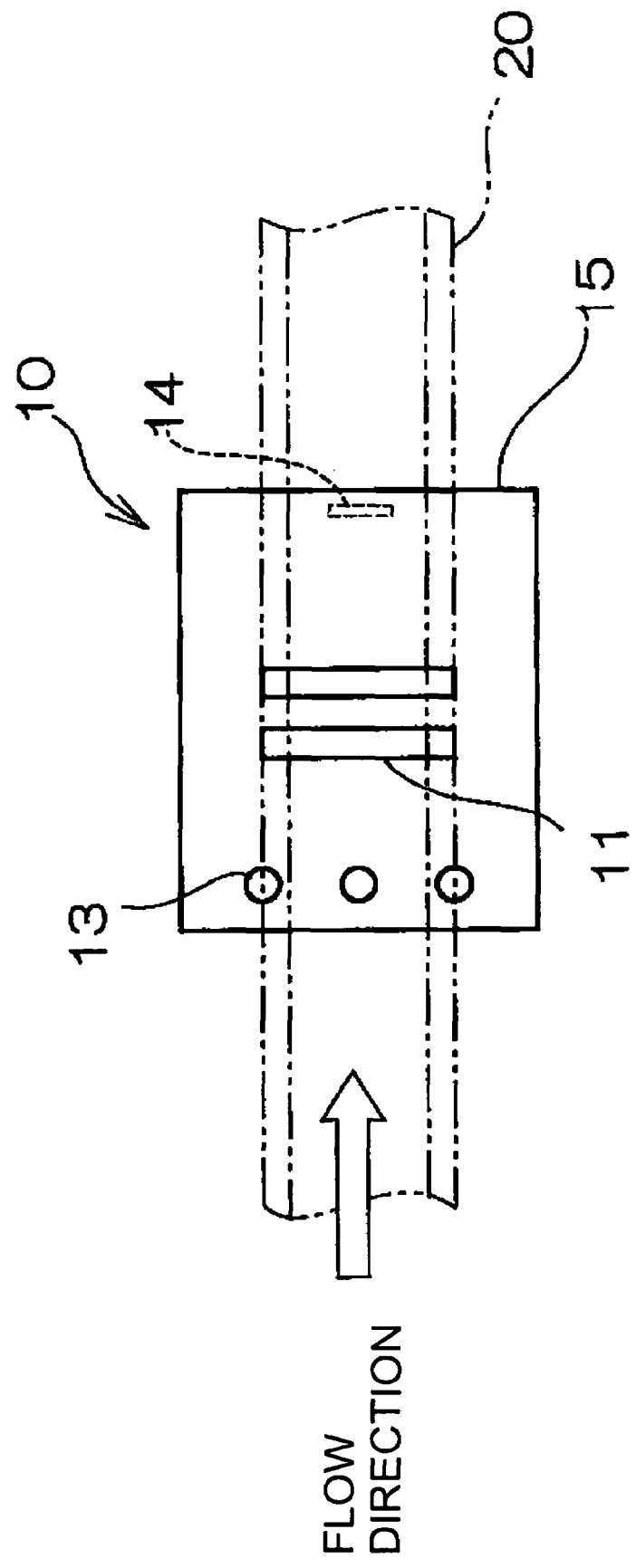
FIG. 2 is a side view of a magnetic sensor used for a detection method of the invention viewed from the terminal side.

Outline of the detection method of the invention will be described with reference to drawings. FIG. 1 shows a cross section of an example of a magnetic sensor used for the detection method of the invention. The magnetic sensor 10 shown in FIG. 1 comprises a magnetoresistive element 11, a permanent magnet 12, a terminal pin 13, a FG (frame ground) terminal pin 14, a holder 15 and a mold material 16. A cover may be optionally attached to the magnetic sensor. The entire measuring part including the magnetic sensor may be housed in an external noise shielding case. FIG. 2 shows the magnetic sensor 10 shown in FIG. 1 seen from the terminal side, wherein the magnetic sensor is disposed on a flow channel 20 in which a liquid to be detected is flowing. The direction of the flow of the liquid mixture is shown by an arrow in FIG. 2. The magnetic particles to be detected that are the bound magnetic nano-particles passing through the magnetic sensor 10 are detected by measuring the change in magnetic resistance. The principle of the detection will be described below.

The flow passageway of an electric current is bent by a Lorentz force from a magnetic field when the magnetic field is applied in a vertical direction of the surface of a semiconductor plate such as an InSb plate, and the resistance increases due to the elongated passageway of the electric current (magnetoresistive effect). Magnetic particles having a size of a critical diameter for superparamagnetism or less (nano-particles) exhibit superparamagnetism even when the substance of the nano-particles is ferromagnetic, and the nano-particles give little magnetoresistive effect even when passing through the magnetic sensor since the particles are hardly responsive to the magnet. On the contrary, magnetic domains are aligned in a given direction by the external magnetic field in magnetic particles having a particle diameter larger than the critical particle diameter (including the bound magnetic nano particles). It is considered that the bound magnetic nano particle has an increased apparent volume due to binding, so that the diameter of the particle exceeds the critical diameter necessary for exhibiting superparamagnetism and the particles tend to become ferromagnetic by magnetization. Consequently, when allowing magnetic particles having a diameter larger than the critical diameter (bound magnetic nano-particles) to pass through the magnetic sensor, the resistance changes due to a magnetoresistive effect. Accordingly, it is possible to selectively detect the bound magnetic nano-particles and thereby indirectly detect the target compound through monitoring the change.

The magnetic sensor will be described below. A semiconductor having high electron mobility is used for the magnetoresistive element. Compound semiconductors of group III-group V elements such as InSb, InAs and GaAs are preferable as the material of the semiconductor, and an n type InSb, which has an electron mobility of as large as 78,000 cm$^2$/V·s, is particularly preferable among them. It is preferable that the magnetoresistive element has a two-terminal structure, and is formed into a meander structure having many electrodes on the surface of the semiconductor on a magnetic or nonmagnetic substrate so that high resistance and high output can be obtained.

Figure 3:
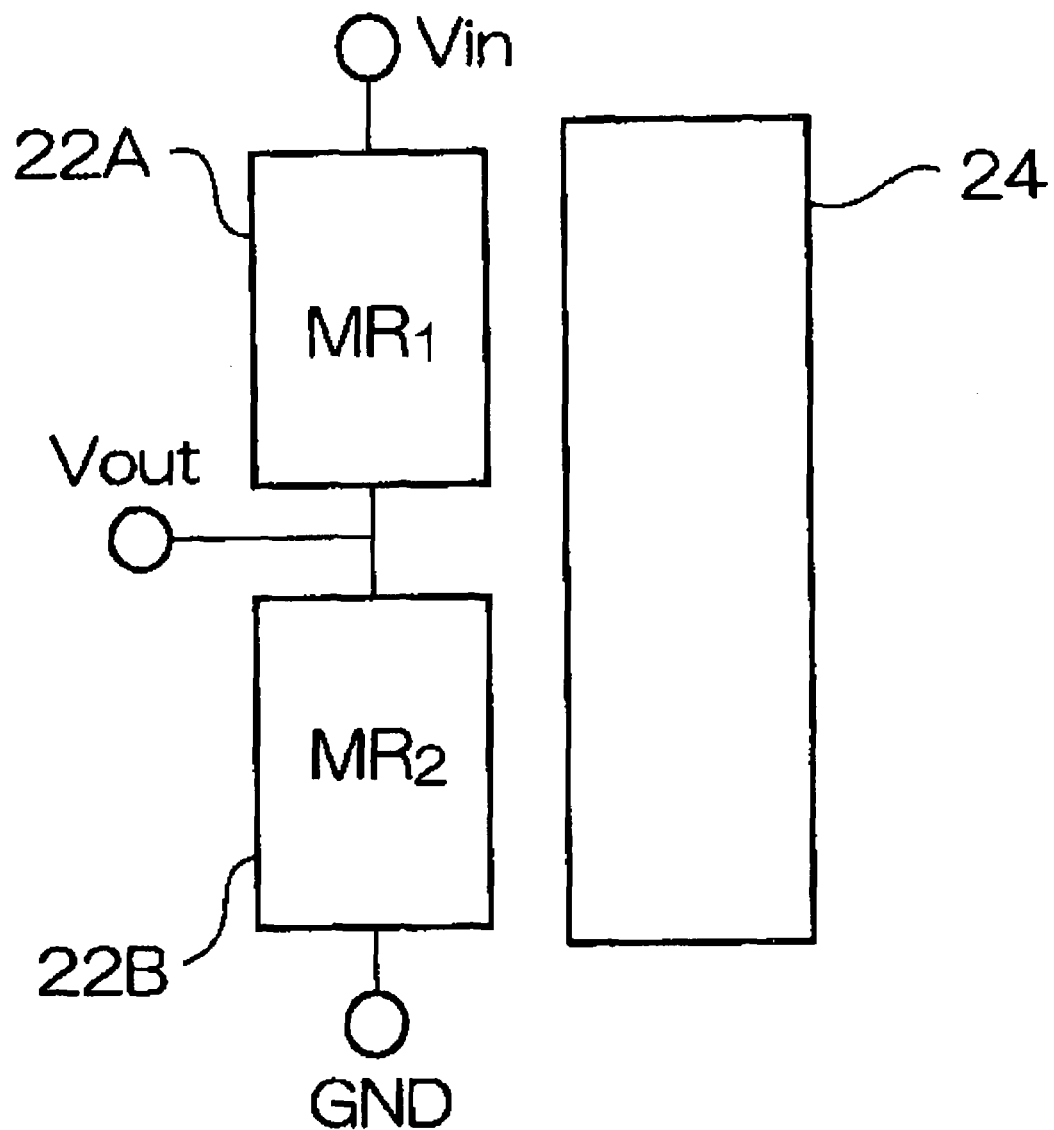
FIG. 3 shows a circuit structure of a magnetic sensor used for a detection method of the invention.

The magnetic sensor circuit is desirably configured by a bias type combination of a magnetoresistive element and a permanent magnet. The circuit configuration may be a single element type configuration having one magnetoresistive element, a two-element type configuration having two elements configured in series, or a four-element type configuration in which the above configurations are bridged. FIG. 3 shows a two-element bias type configuration as a representative example. In FIG. 3, two magnetoresistive elements 22A and 22B are arranged in series with a permanent magnet 24 disposed close to the two magnetoresistive elements 22A and 22B.

Figure 4B:
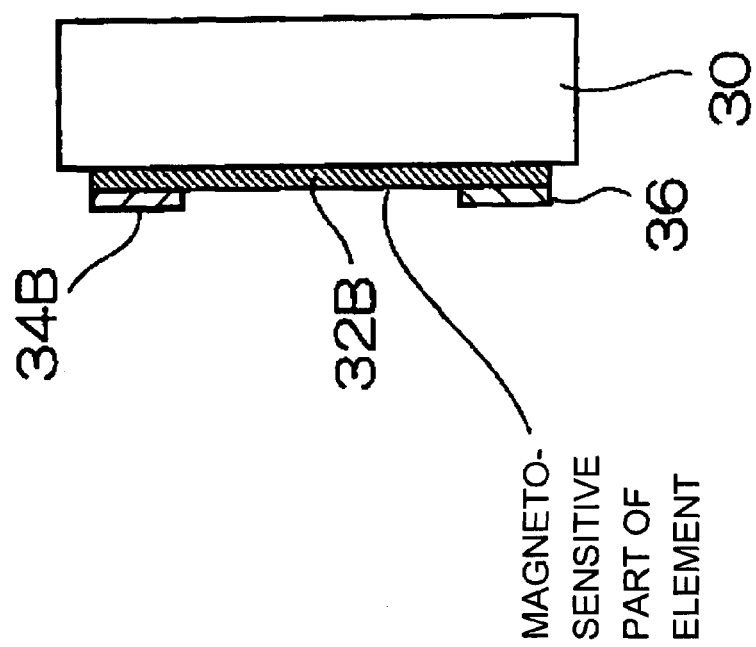
FIGS. 4A and 4B show the size of detection elements of a magnetic sensor used for a detection method of the invention.
Figure 4A:
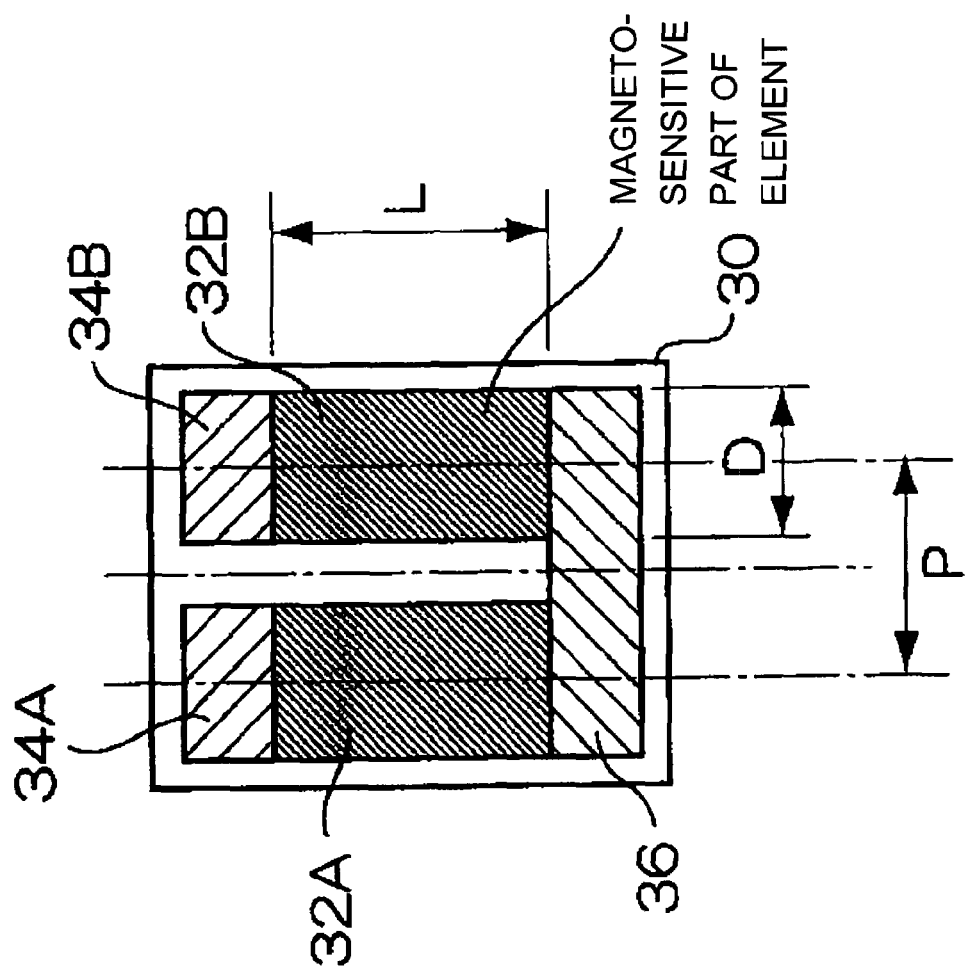

A preferable size of detection elements will be described below using a two-element type configuration as an example. FIGS. 4A and 4B show a detection part of the two-element type magnetic sensor, where FIG. 4A shows a plane view and FIG. 4B shows a side view. The detection part shown in FIGS. 4A and 4B comprises two magnetoresistive elements (magnetosensitive parts of the elements) 32A and 32B disposed on the substrate 30, and electrodes 34A and 34B are bonded to one ends of the magnetoresistive elements 32A and 32B, respectively. An electrode 36 is bonded to the other ends of the magnetoresistive elements 32A and 32B so as to bridge the magnetoresistive elements.

In FIGS. 4A and 4B, the pitch P between the elements is preferably from 10 to 5,000 μm, particularly preferably from 100 to 1,000 μm; the width D of the elements is preferably from 1 to 1,000 μm, particularly preferably from 10 to 500 μm; and the detection width L is preferably from 0.01 to 10 mm, particularly preferably from 0.05 to 3 mm, which is preferably close to the inner diameter of the flow channel described below.

The surface magnetic flux density of the permanent magnet is preferably from 0.01 to 10 T, more preferably from 0.05 to 1 T, in terms of sensitivity of the element and practical applicability.

When the concentration of the target compound in the test liquid in the invention is low, the measurement with the magnetic sensor can be carried out after allowing the target compound to bind to the magnetic nano-particles and concentrating the formed bound magnetic nano-particles by magnetic separation. The magnet used for magnetic separation may be either a permanent magnet or an electromagnet, and the surface magnetic flux density thereof is desirably from 0.05 to 1 T. A given volume (for example, from 0.05 to 10 mL, at a flow rate of 0.001 to 100 mL/minute) of the concentrated dispersion liquid may be injected into the flow channel (to be described below) disposed on the surface of the magnetic sensor, so that the bound magnetic nano particles can be detected and thereby the target compound can be indirectly detected.

While the concentration after the concentration process may be optimized according to the measuring conditions since the concentration is different depending on the kind and size of the target compound, the number of ligands bound to the magnetic nano-particles, the size of the magnetic nano-particles and sensitivity of the magnetic sensor, the concentration is, for example, preferably 0.1 mM or more.

In the invention, the flow channel preferably has a cross section of from 10 to $10^7$ μm$^2$, more preferably from $10^2$ to $10^6$ μm$^2$. A thinner thickness at the magnetic sensor side is preferable so long as the strength is sufficient, and the thickness is preferably from 10 to 500 μm. The cross section is not restricted to a circle, and an ellipsoid or a rectangular shape may be used. The material of the flow channel is not particularly restricted so long as it does not affect the magnetic field, and preferable examples thereof include glass, silicone resign, fluorinated resins such as Teflon®, polyethylene and polypropylene. The surface of the inner wall of the flow channel may be appropriately coated in order to prevent components in the test liquid from adhering and bound magnetic nano-particles from clogging.

After injecting from 0.1 to 1,000 μL, preferably from 0.2 to 100 μL of the test liquid into the colloid solution of the magnetic nano-particles flowing in the flow channel at a flow rate from 0.001 to 100 mL/minute, preferably from 0.002 to 10 mL/minute, the resulting liquid mixture (a dispersion liquid containing the bound magnetic nano-particles) is allowed to pass just above the detection element of the magnetic sensor, whereby the magnetic flux changes, and the accompanying change in magnetoresistance is detected. While the test liquid may be injected either continuously or pulse-wise, the pulse-wise injection is preferable in terms of sensitivity of detection. Micro-reactors disclosed in JP-A Nos. 2005-288254, 2005-46651 and 2005-46652, the disclosures of which are incorporated by reference herein, may be used for injection and mixing of the test liquid. While the distance from the mixing part (dispersion liquid) to the magnetic sensor may be adjusted, depending on the binding reaction rate between the target compound and magnetic nano-particles, flow rate and cross-section of the flow channel, the distance is preferably 1 mm or less, more preferably 0.5 mm or less, in order to secure a given level or more of detection sensitivity.

Figure 5:
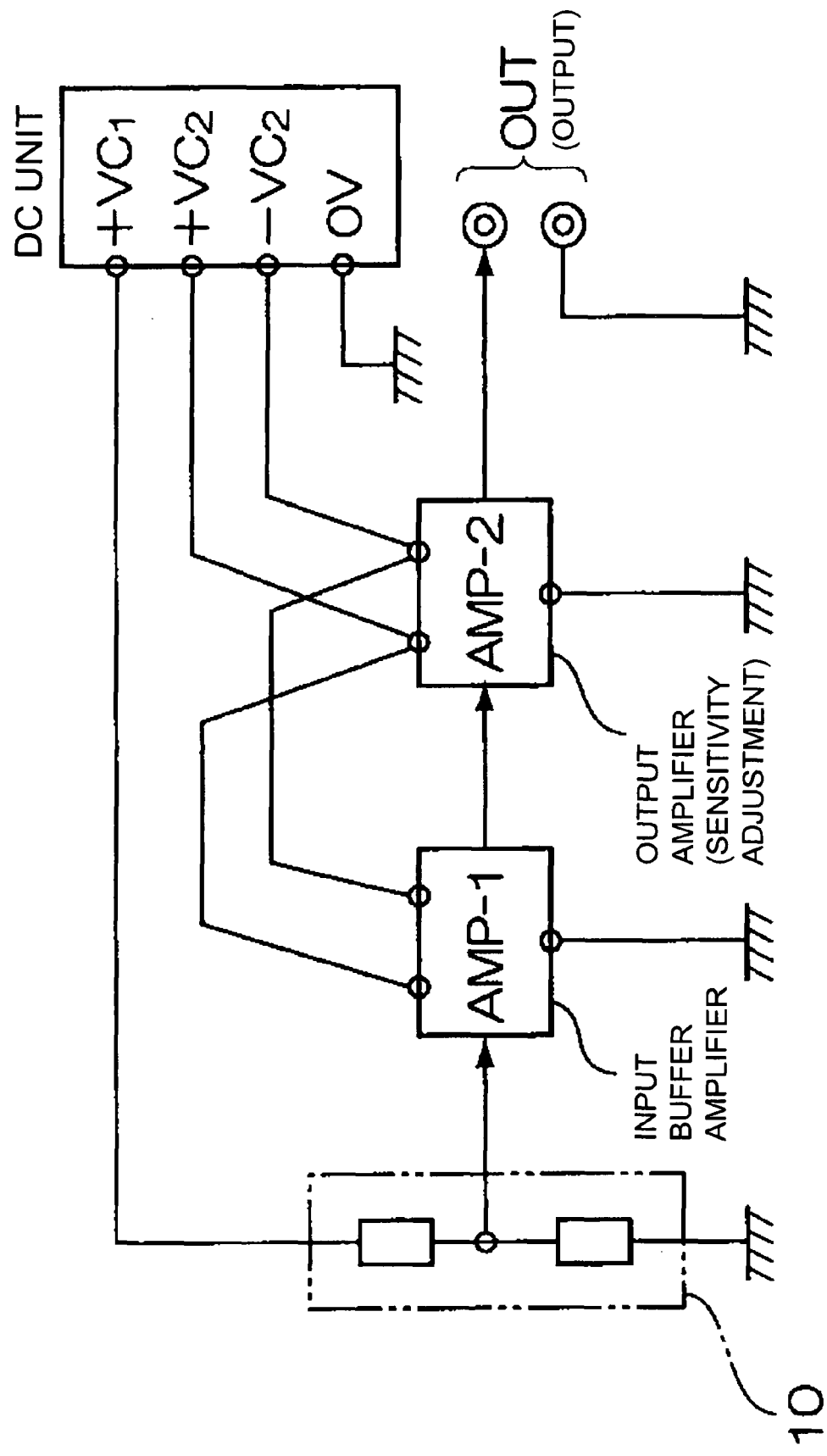
FIG. 5 is a block diagram of a measuring circuit used for a detection method of the invention.

FIG. 5 shows a block diagram of the measuring circuit that can be used in the detection method of the invention. Since the output voltage from the magnetic sensor 10 is proportional to the power source voltage and the change of resistance, the output voltage is increased in proportion to the concentration of the bound magnetic nano-particles. The output voltage is amplified with an amplifying circuit (output amplifier) and is monitored. A buffer amplifier (input buffer amplifier) is desirably used for the amplifying circuit for suppressing the amplification factor from being affected by the change of the input resistance of the sensor due to temperature change. It is also desirable to apply an appropriate intensity of a bias magnetic field so that the relation between the magnetic flux density and resistance changes falls within a linear range.

The magnetic sensor may be a multi-channel sensor for simultaneous measurement of various target compounds.

(Magnetic Nano-Particles)

Magnetic nano-particles having a number average particle diameter from 2 to 50 nm are used for the magnetic nano-particles in the invention. The magnetic nano-particles have a number average particle diameter of 2 nm or more and thus can be reliably prepared while the magnetic nano-particles have a number average particle diameter of 50 nm or less and thus are able to trap a minute quantity of the target compound since the surface area is large. The number average particle diameter of the magnetic nano particles is preferably from 3 to 50 nm, particularly preferably from 5 to 40 nm, in terms of stability and magnetic force of the particles.

The above-described magnetic nano-particles can be prepared according to the method described in Japanese Patent Application National Publication No. 2002-517085, the disclosure of which is incorporated by reference herein. For example, the magnetic nano-particles of iron oxide or ferrite can be formed by placing an aqueous solution containing an iron (II) compound or iron (II) compound and a metal (II) compound in an oxidative condition necessary for forming a magnetic oxide and by maintaining the solution in a pH range of 7 or more. The magnetic nano-particles in the invention can be also obtained by mixing an aqueous solution containing a metal (II) compound and an aqueous solution containing an iron (III) compound in an alkali condition. Otherwise, the magnetic nano-particles can be obtained by the method described in Biocatalysis, 1991, vol. 5, p 61-69, the disclosure of which is incorporated by reference herein. Ferromagnetic ordered alloys such as FePd, FePt, CoPt and FePtCu may be used for the magnetic nano-particles.

The magnetic nano-particles in the invention may be preferably selected from the group consisting of metal oxides such as iron oxide and ferrites (Fe, M)$_3$O$_4$. Examples of iron oxide include magnetite, maghemite and mixtures thereof. In the formula, M denotes a metal ion that is able to form a magnetic metal oxide together with the iron ion, which is typically selected from transition metals, most preferably from $Zn^{2+}$, $Co^{2+}$, $Mn^{2+}$, $Cu^{2+}$, $Ni^{2+}$ and $Mg^{2+}$. The molar ratio of M/Fe is determined according to the stoichiometric composition of the ferrite. While the metal salt is supplied as a solid or in a solution, it is preferably a chloride salt, bromide salt or sulfate salt.

Iron oxide and ferrite are preferable in terms of safety.

Iron preferably exists in two different oxidation states, $Fe^{2+}$ and $Fe^{3+}$, in the solution when forming magnetite. Iron can exist in the two different oxidation states in the solution by adding a mixture of iron (II) salt and iron (III) salt, preferably by adding a little larger mol amount of Fe(II) salt than the mol amount of Fe(III) salt as compared to the proportion of Fe(II) and Fe(III) ions in the desired magnetic oxide; or by adding Fe (II) salt or Fe (III) salt and partially converting the oxidation state of one of $Fe^{2+}$ or $Fe^{3+}$ to the oxidation state of the other iron ion preferably by oxidation or optionally by reduction.

The magnetic metal oxide is preferably aged at a temperature in the range from 30 to 100° C., particularly preferably from 50 to 90° C. The pH of the solution should be 7 or more in order to permit various metal ions to interact to one another for forming the magnetic metal oxide. The pH is maintained in a desired range by using an appropriate buffer solution as an aqueous solution when initially adding the metal salts, or by adding a base to the solution after adjusting to a required oxidation state. Once a specified pH has been selected in a range of 7 or more, the pH is preferably maintained throughout the entire process for preparing the magnetic nano-particles in order to secure a substantially uniform distribution of the particle diameter of the final product.

A process for adding additional metal salts to the solution may be provided in order to control the particle diameter of the magnetic nano-particles. This process may be performed in two different operation methods. One method is a stepwise increasing method, which is called a stepwise method hereinafter, wherein respective components (metal salts, an oxidant and a base) are added several times, preferably in the same amount every time, to the solution in a predetermined order, and the step is repeated until nano-particles having a desired size are obtained. The amount of addition in each time is determined so that polymerization of the metal ions can be substantially avoided in the solution (except on the surface of the particles).

The other method is a continuous addition method, wherein respective components (metal salts, an oxidant and a base) are continuously added to the solution in a predetermined order at a substantially uniform flow rate for each component in order to substantially avoid the metal ions from being polymerized in the solution except on the surface of the particles. Particles having a narrow distribution of the size can be formed by using the above-mentioned stepwise or continuous method.

Ligands to be described below can be bound to the magnetic nano-particles by attaching molecules having a functional group (surface modification agent) on the surface of the particles. Such a molecule may be a low molecular weight compound such as an amino acid (for example L-glutamic acid or aspartic acid) or a carboxylic acid (for example citric acid, tartaric acid or oleic acid), or a polymer such as polysaccharide, protein, peptide or polyamine, or ω-silane: $Si(OR)_3(CH_2)_nX$ (in the formula, R represents an alkyl group, n is an integer from 1 to 18 (including 1 and 18), and X is a functional group selected from the group consisting of $NH_2$, CN and SH). The ligand can be bound using the functional group such as amino, carboxyl or hydroxyl group provided by the above-mentioned molecules. Otherwise, one terminal of the molecule may be activated into a succinamide ester. The magnetic particles the surface of which is modified with a compound having a functional group are stable as a colloid solution, which enables bonding of the ligand described below to be manipulated as a solution reaction.

<Ligand>

Ligands are preferably used for permitting the magnetic nano-particles in the invention to bind to the target compound to be described below. In other words, it is preferable that the magnetic nano-particles according to the invention bear the ligand for specifically binding to the target compound on the surface of the particles. The ligand is preferably a molecule having a tendency to bind to (or having reactivity with) the target compound. Such a molecule may be linked to an external stimulation-responsive compound.

When the target compound is a biological molecule, the ligand used may be a biological molecule. For example, when the target compound is an antigen, an antibody may be used as the ligand.

A complex-forming compound having a chelating ability to a specified metal ion may also be used as the ligand.

—Biological Molecule—

Examples of the biological molecule include nucleic acids, antigens and antibodies (monoclonal or polyclonal), peptides and other proteins, polysaccharides, enzymes or substrates thereof, compounds such as lipids, and microorganisms such as viruses or bacteria or a part thereof.

Nucleic acids denotes deoxyribonucleic acids (DNAs) and ribonucleic acids (RNAs) in a narrow sense, and may include PNA (peptide nucleic acids) in a wide sense. Examples of the RNAs include mRMA, tRNA and rRNA. Examples of the nucleic acids also include fragments of the DNA and RNA, not only complete DNAs and RNAs.

Such ligands may exist as a part of the surface of the magnetic nano-particles, or may be directly or indirectly provided on the surface of the magnetic nano-particles.

<Target Compound>

The target compound is a substance to be detected in the invention, and is a synonym of a target substance. The target compound is bound to the magnetic nano-particles via the ligand bound to the magnetic nano-particles, and forms the bound magnetic nano-particles. While the target compound is not particularly restricted, it is preferably the above-mentioned biological molecule.

When the target compound is a nucleic acid, for example, a transcription control factor that is able to control transcription of various base sequences may be selectively trapped from various proteins, or DNA fragments having different base sequences may be promptly and easily detected by designing complementary base sequences.

Otherwise, a target compound that interacts with the ligand and is able to form a complex with the magnetic nano-particles may be readily detected.

EXAMPLES

While the invention is described below with reference to examples, the invention is by no means restricted to these examples. "%" in the examples is based on the mass unless otherwise stated.

Example 1

(Detection of Avidin-Bound Liposome Using Biotinylated Magnetic Nano-Particles)

A protein was bound on the surface of liposome using SPDP (Peter Walden, Zoltan A. Nagy and Jan Klein, J. Mol. Immunol., 2, 191-197(1986), the disclosure of which is incorporated by reference herein), and detection using magnetic nano-particles was carried out as follows.

(1) Preparation of Dispersion Liquid of Magnetic Nano-Particles

Iron (III) chloride hexahydrate (10.8 g) and iron chloride (II) tetrahydrate (6.4 g) were each dissolved in 80 mL of 0.5 mol/L (0.5 N) aqueous hydrochloric acid solution, and mixed. Aqueous ammonia (96 mL; 14% by mass) was added to the resulting solution at a rate of 2 mL/minute with stirring. The solution was heated at 80° C. for 60 minutes followed by cooling to room temperature. Aggregates obtained were purified with water by magnetic separation. The aggregate was confirmed to be magnetite ($Fe_3O_4$) with a crystal size of about 10 nm by X-ray diffraction. A dispersion liquid (pH 5) of the magnetic nano-particles was prepared by dispersing the aggregate in 200 mL of an aqueous solution in which 2.3 g of polyoxyethylene (4.5) lauryl ether acetate was dissolved.

(2) Preparation of Avidin-Bound Liposome

Dipalmitoyl phosphatidyl ethanolamine (DPPE), N-succimidyl-3-(2-pyridyldithio)propionate (SPDP) and triethylamine were dissolved in methanol-chloroform (9:1) in a molar ratio of 1:2:2, and were allowed to react at room temperature for 2 hours. After the reaction, the product was washed with phosphate buffer (100 mM, pH 7.2) and dried in nitrogen stream to obtain dithiopyridine-dipalmitoyl phosphatidyl ethanolamine (DTP-DPPE). The product was mixed with dipalmitoyl phosphatidyl choline (DPPC) in a ratio of DPPE to DPPC of 2:8. The mixture was dissolved in methanol-chloroform, and was formed into a thin film by drying in nitrogen stream. Then, the thin film was dispersed in phosphate buffer (PBS; pH 7.2), and DTP liposome (lipid concentration: 25 μM/mL) with an average particle diameter of 120 nm was obtained by ultrasonic irradiation and filtration.

Avidin and SPDP (molar ratio 1:1) were allowed to react in 100 mM of carbonate buffer containing 150 mM NaCl (pH 8.0) for 1 hour. After reducing disulfide by adding dithiothreitol (DTT, 5 mM), the reaction product was purified with Sephadex G-25 and added to the DTP liposome solution. The purified product was separated by sucrose gradient centrifugation and was re-dispersed in 100 mM of phosphate buffer (pH 7.2) to obtain an avidin-bound liposome solution.

(3) Preparation of Biotinylated Magnetic Nano-Particles

An MES buffer solution (7.5 mL; 0.1 M, pH 6.0) was added to 2.5 mL of the dispersion liquid of the magnetic nano-particles, and 19 mg of WSC (water-soluble carbodiimide) and 18 mg of N-hydroxysulfosuccimide (sulfo-NHS) were added at room temperature and stirred for 30 minutes. Biotin-PEO-Amine (28 mg, manufactured by Pierce) was added to the solution, which was boiled overnight. After stopping the reaction by adding 200 μL of 1 M Tris/HCl (pH 8.0), the product was purified with a PD-10 column (manufactured by Amersham-Bioscience) to obtain a solution of biotinylated magnetic nano-particles.

(4) Detection of Avidin-Bound Liposome Using Biotinylated Magnetic Nano-Particles To 50 mL of a 10 times diluted solution of the biotinylated magnetic nano-particles solution were added 5 mL of a 100 times diluted solution of the avidin-bound liposome solution (sample A), a 50 times diluted solution of the avidin-bound liposome solution (sample B) and a 20 times diluted solution of the avidin-bound liposome solution (sample C), and each solution was stirred for 10 minutes. Each solution was concentrated to 5 mL by magnetic separation using a magnet having a surface magnetic a surface flux density of 0.3 T. These solutions (10 μL, samples A to C) were injected into a polystyrene flow channel with an inner diameter of 0.5 mm (cross section; about $2 \times 10^5$ μm$^2$) and a thickness of 0.2 mm at a flow rate of 20 μL/second, and an output voltage of each sample was measured using a magnetic sensor. The results are shown in FIG. 6. The magnetic sensor used is a two-element bias type magnetic sensor containing InSb as a magnetoresistive element with an inter-element pitch P of 0.75 mm, an element width D of 0.3 mm, a detection length L of 3 mm and a surface magnetic flux density of the permanent magnet of 0.45 T. The distance between the magnetic sensor and the dispersion liquid flowing in the polystyrene flow channel was 0.4 mm. It was found from FIG. 6 that the output voltage is approximately proportional to the concentration of the avidin-bound liposome. The average particle diameter of the avidin-bound liposome bound to the biotinylated magnetic nano-particles was 260 nm.

Example 2

A solution (L1) of the biotinylated magnetic nano-particles used in Example 1, which was diluted 10 times, was allowed to continuously flow from the fluid feed channel 26 at a flow rate of 5 mL/minute using a micro-mixer described in JP-A No. 2005-46652. A 5 times diluted solution (sample D) or a 10 times diluted solution (sample E) of the above-mentioned avidin-bound liposome solution (L2) was injected from the fluid feed channel 28 for 5 seconds at a flow rate of 1 mL/minute (injection volume; 83 μL). The solutions L1 and L2 were mixed while they pass through a reaction flow channel 22 (cross section: about $7 \times 10^5$ μm$^2$), and the liquid mixture (LM) was introduced into a micro-flow channel (cross section: about $8 \times 10^5$ μm$^2$) from a discharge channel 32 (cross section: about $8 \times 10^5$ μm$^2$) to measure the output voltage using a magnetic sensor. An output voltage approximately proportional to the concentration of the avidin-bound liposome was obtained. The magnetic sensor used is a single-element type magnetic sensor containing InSb as a magnetoresistive element with an element width D of 0.3 mm, a detection length L of 1 mm and a surface magnetic flux density of the permanent magnet of 0.45 T. The distance between the magnetic sensor and the dispersion liquid flowing in the flow channel was 0.5 mm.

The present invention provides at least the following embodiments 1 to 18.

1. A method for detecting a target compound comprising:
injecting a test liquid containing a target compound into a colloid solution of magnetic nano-particles having an average particle diameter of 50 nm or less to allow the target compound to bind to the magnetic nano-particles, thereby forming bound magnetic nano-particles having a diameter of 100 nm or more; and
bringing a dispersion liquid containing the bound magnetic nano-particles in proximity to a magnetic sensor comprising at least a magnetoresistive (MR) element and a permanent magnet while measuring the change in magnetic resistance to selectively detect the bound magnetic nano-particles, thereby indirectly detecting the target compound.

2. The method of embodiment 1, wherein the magnetic nano-particles have, on the surface thereof, a ligand for specifically binding to the target compound.

3. The method of embodiment 1, wherein the distance between the magnetic sensor and the dispersion liquid is 1 mm or less when the dispersion liquid is brought in proximity to the magnetic sensor.

4. The method of embodiment 1, wherein the surface magnetic flux density of the permanent magnet is from 0.01 to 10 T.

5. The method of embodiment 1, wherein the magnetoresistive element contains an n-type InSb semiconductor.

6. The method of embodiment 1, wherein the magnetic nano-particles comprise iron oxide or ferrite.

7. A method for detecting a target compound comprising:
injecting a test liquid containing a target compound into a colloid solution of magnetic nano-particles having an average particle diameter of 50 nm or less to allow the target compound to bind to the magnetic nano-particles, thereby forming bound magnetic nano-particles having a diameter of 100 nm or more;
concentrating the formed bound magnetic nano-particles by magnetic separation, thereby obtaining a concentrated dispersion liquid of the bound magnetic nano-particles; and
bringing the concentrated dispersion liquid in proximity to a magnetic sensor comprising at least a magnetoresistive (MR) element and a permanent magnet while measuring the change in magnetic resistance to selectively detect the bound magnetic nano-particles, thereby indirectly detecting the target compound.

8. The method of embodiment 7, wherein the magnetic nano-particles have, on the surface thereof, a ligand for specifically binding to the target compound.

9. The method of embodiment 7, wherein the distance between the magnetic sensor and the dispersion liquid is 1 mm or less when the dispersion liquid is brought in proximity to the magnetic sensor.

10. The method of embodiment 7, wherein the surface magnetic flux density of the permanent magnet is from 0.01 to 10 T.

11. The method of embodiment 7, wherein the magnetoresistive element contains an n-type InSb semiconductor.

12. The method of embodiment 7, wherein the magnetic nano-particles comprise iron oxide or ferrite.

13. A method for detecting a target compound comprising:
injecting from 0.1 to 1000 μL of a test liquid containing a target compound into a colloid solution of magnetic nano-particles having an average particle diameter of 50 nm or less, the colloid solution flowing at a flow rate from 0.001 to 100 mL/minute in a flow channel having a cross section from 10 to $10^7$ μm$^2$, to allow the target compound to bind to the magnetic nano-particles, thereby forming bound magnetic nano-particles having a diameter of 100 nm or more; and
bringing the resulting liquid mixture containing the bound magnetic nano-particles in proximity to a magnetic sensor comprising at least a magnetoresistive (MR) element and a permanent magnet while measuring the change in magnetic resistance to selectively detect the bound magnetic nano-particles, thereby indirectly detecting the target compound.

14. The method of embodiment 13, wherein the magnetic nano-particles have, on the surface thereof, a ligand for specifically binding to the target compound.

15. The method of embodiment 13, wherein the distance between the magnetic sensor and the dispersion liquid is 1 mm or less when the dispersion liquid is brought in proximity to the magnetic sensor.

16. The method of embodiment 13, wherein the surface magnetic flux density of the permanent magnet is from 0.01 to 10 T.

17. The method of embodiment 13, wherein the magnetoresistive element contains an n-type InSb semiconductor.

18. The method of embodiment 13, wherein the magnetic nano-particles comprise iron oxide or ferrite.

Therefore, according to the invention, the target compound in the liquid mixture can be simply and efficiently detected without trapping the magnetic nano-particles.

What is claimed is:

1. A method for detecting a target compound comprising:
    injecting a test liquid containing a target compound into a colloid solution of magnetic nano-particles having an average particle diameter of 50 nm or less to allow the target compound to bind to the magnetic nano-particles, thereby forming bound magnetic nano-particles having a diameter of 100 nm or more;
    concentrating the formed bound magnetic nano-particles by magnetic separation, thereby obtaining a concentrated dispersion liquid of the bound magnetic nano-particles;
    bringing the concentrated dispersion liquid containing the bound magnetic nano-particles and non-bound magnetic nano-particles in proximity to a magnetic sensor comprising at least a magnetoresistive (MR) element and a permanent magnet; and
    measuring the change in magnetic resistance to selectively detect the bound magnetic nano-particles in a dispersed state in the concentrated dispersion liquid without trapping the bound and the non-bound magnetic nano-particles, thereby indirectly detecting the target compound.

2. The method of claim 1, wherein the magnetic nano-particles have, on the surface thereof, a ligand for specifically binding to the target compound.

3. The method of claim 1, wherein the distance between the magnetic sensor and the dispersion liquid is 1 mm or less when the dispersion liquid is brought in proximity to the magnetic sensor.

4. The method of claim 1, wherein the surface magnetic flux density of the permanent magnet is from 0.01 to 10 T.

5. The method of claim 1, wherein the magnetoresistive element contains an n-type InSb semiconductor.

6. The method of claim 1, wherein the magnetic nano-particles comprise iron oxide or ferrite.

7. A method for detecting a target compound comprising:
    injecting from 0.1 to 1000 μL of a test liquid containing a target compound into a colloid solution of magnetic nano-particles having an average particle diameter of 50 nm or less, the colloid solution flowing at a flow rate from 0.001 to 100 mL/minute in a flow channel having a cross section from 10 to $10^7$ μm$^2$, to allow the target compound to bind to the magnetic nano-particles, thereby forming bound magnetic nano-particles having a diameter of 100 nm or more;
    concentrating the formed bound magnetic nano-particles by magnetic separation, thereby obtaining a concentrated dispersion liquid of the bound magnetic nano-particles;
    bringing the concentrated dispersion liquid containing the bound magnetic nano-particles and non-bound magnetic nano-particles in proximity to a magnetic sensor comprising at least a magnetoresistive (MR) element and a permanent magnet; and
    measuring the change in magnetic resistance to selectively detect the bound magnetic nano-particles in a dispersed state in the concentrated dispersion liquid without trapping the bound and the non-bound magnetic nano-particles, thereby indirectly detecting the target compound.

8. The method of claim 7, wherein the magnetic nano-particles have, on the surface thereof, a ligand for specifically binding to the target compound.

9. The method of claim 7, wherein the distance between the magnetic sensor and the dispersion liquid is 1 mm or less when the dispersion liquid is brought in proximity to the magnetic sensor.

10. The method of claim 7, wherein the surface magnetic flux density of the permanent magnet is from 0.01 to 10 T.

11. The method of claim 7, wherein the magnetoresistive element contains an n-type InSb semiconductor.

12. The method of claim 7, wherein the magnetic nano-particles comprise iron oxide or ferrite.

* * * * *